(12) United States Patent
Wizel et al.

(10) Patent No.: US 7,563,930 B2
(45) Date of Patent: Jul. 21, 2009

(54) CRYSTAL FORMS OF CINACALCET HCl AND PROCESSES FOR THEIR PREPARATION

(75) Inventors: Shlomit Wizel, Petah Tiqva (IL); Revital Lifshitz-Liron, Hertzlia (IL); Sharon Avhar-Maydan, Givataym (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 58 days.

(21) Appl. No.: 11/605,149

(22) Filed: Nov. 22, 2006

(65) Prior Publication Data

US 2007/0185211 A1      Aug. 9, 2007

Related U.S. Application Data

(60) Provisional application No. 60/739,215, filed on Nov. 22, 2005, provisional application No. 60/742,626, filed on Dec. 5, 2005.

(51) Int. Cl.
*C07C 211/00* (2006.01)

(52) U.S. Cl. .................. 564/337; 564/336; 560/41; 560/28; 514/487; 514/649

(58) Field of Classification Search .................. 564/337, 564/336; 560/41, 28; 514/487, 649
See application file for complete search history.

(56) References Cited

U.S. PATENT DOCUMENTS

| 4,966,988 | A | 10/1990 | Schinski et al. |
| 5,648,541 | A | 7/1997 | Van Wagenen et al. |
| 6,011,068 | A | 1/2000 | Nemeth et al. |
| 6,031,003 | A | 2/2000 | Nemeth et al. |
| 6,211,244 | B1 | 4/2001 | Van Wagenen et al. |
| 6,313,146 | B1 | 11/2001 | Van Wagenen et al. |
| 2005/0147669 | A1* | 7/2005 | Lawrence et al. ............ 424/464 |
| 2005/0234261 | A1 | 10/2005 | Wilken et al. |
| 2006/0276534 | A1 | 12/2006 | Martin et al. |

FOREIGN PATENT DOCUMENTS

WO    WO 2006/125026    11/2006

OTHER PUBLICATIONS

Anonymous, "N-[1-(R)-(-)(1-naphthyl)]-3-[3-[3-(trifluoromethyl)phenyl}-1-aminopropane hydrochloride", IP.COM Journal, May 23, 2005, XPO002424259.
Devasher et al., "Aqueous-Phase, Palladium-catalyzed cross-coupling of aryl bromides under mild conditions, using water soluable, sterically demanding alkylphosphines", Journal of Organic Chemistry, American Chemical Society, vol. 69, 2004, pp. 7919-7927.
Database Belistein; Belistein Institute for Organic Chemistry, Frankfurt-Main, DE; XP002451055 (& Pharmazie, vol. 59, No. 10, 2004, pp. 744-752).
"Sensipar (Cinacalcet HCl) Tablets" Summary Basis of Approval of New Drug Application #21-688 By FDA, (2004).
J. Iqbal, et al. "Cinacalcet Hydrochloride" *IDrugs*, vol. 6, No. 6, p. 587-592, (2003).
L.A. Sorbera, et al. "Cinacalcet Hydrochloride" *Drugs of the Future*, vol. 27, No. 9, p. 831-836, (2002).
X. Wang, et al. "Synthesis of Cinacalcet Congeners" *Tetrahedron Letters*, vol. 45, p. 8355-8358, (2004).
Snyder, L.R. et al., *Introduction To Modern Liquid Chromatography*, 2nd Ed., (1979), pp. 549-572, John Wiley & Sons, Inc.
Strobel, H.A. et al., *Chemical Instrumentation: A Systematic Approach*, 3rd Ed., (1989), pp. 391-393, 879-894, 922-925, 953.

* cited by examiner

*Primary Examiner*—Karl J Puttlitz
*Assistant Examiner*—Sudhakar Katakam
(74) *Attorney, Agent, or Firm*—Kenyon & Kenyon LLP

(57) ABSTRACT

Provided are crystalline forms of Cinacalet HCl and processes for their preparation.

37 Claims, 6 Drawing Sheets

CRYSTAL FORMS OF CINACALCET HCl AND PROCESSES FOR THEIR PREPARATION

CROSS-REFERENCE TO RELATED APPLICATIONS

This application claims the benefits of U.S. Provisional Patent Application Ser. Nos. 60/739,215, filed Nov. 22, 2005 and 60/742,626, filed Dec. 5, 2005, hereby incorporated by reference.

FIELD OF INVENTION

The present invention relates to novel crystalline forms of Cinacalcet HCl.

BACKGROUND OF THE INVENTION (R)-α-methyl-N-[3-[3-(trifluoromethyl)phenyl]propyl]-1-naphthalenemethane amine is known as Cinacalcet. The Cinacalcet hydrochloride has the molecular formula $C_{22}H_{22}F_3N \cdot HCl$, a molecular weight of 393.9 and the chemical structure:

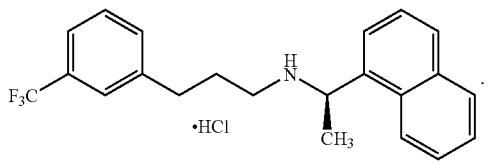

The CAS number for the hydrochloride is 364782-34-3, and that of the free base is 226256-56-0.

Cinacalcet is marketed as SENSIPAR™ (Amgen, USA), and is the first drug in a class of compounds known as calcimimetics to be approved by the FDA. Cinacalcet is approved for treatment of secondary hyperparathyroidism in patients with chronic kidney disease on dialysis. Elevated levels of parathyroid hormone (PTH), an indicator of secondary hyperparathyroidism, are associated with altered metabolism of calcium and phosphorus, bone pain, fractures, and an increased risk for cardiovascular death.

Calcimimetics are a class of orally active, small molecules that decrease the secretion of PTH by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Treatment with Cinacalcet lowers serum levels of PTH as well as the calcium/phosphorus ion product, a measure of the amount of calcium and phosphorus in the blood, which, when elevated, causes harmful deposition of calcium in various parts of the body.

U.S. Pat. No. 6,011,068 discloses calcium receptor-active molecules, such as those having the general structure of Cinacalcet. U.S. Pat. No. 6,211,244 discloses calcium receptor-active compounds related to Cinacalcet and methods of making such compounds. Cinacalcet and its enantiomer may be produced by various methods, using the processes disclosed in U.S. Pat. No. 6,211,244, Drugs of the Future, 27 (9), 831 (2002) and U.S. Pat. No. 5,648,541.

The present invention relates to the solid state physical properties of Cinacalcet hydrochloride. These properties can be influenced by controlling the conditions under which Cinacalcet hydrochloride is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences, as it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

The discovery of new polymorphic forms of a pharmaceutically useful compound and of processes of preparing such polymorphic forms provides opportunities to improve the performance characteristics of a pharmaceutical product. Such discoveries enlarge the repertoire of materials that a formulation scientist has available for designing, for example, a pharmaceutical dosage form of a drug with a targeted release profile or other desired characteristic. Thus, the present invention presents new crystalline forms of Cinacalcet HCl to the pharmaceutical sciences.

SUMMARY OF THE INVENTION

In one embodiment, the invention is directed to crystalline form of Cinacalcet HCl, herein defined as form II, characterized by a powder XRD pattern, having four x-ray powder diffraction peaks selected from the following: about 10.6°, 13.9°, 16.4°, 17.1°, and 21.6°±0.2° 2θ. The crystalline form of Cinacalcet HCl may have x-ray powder diffraction peaks at about 10.6°, 13.9°, 17.1°, and 21.6°±0.2° 2θ. Alternatively, the crystalline form of Cinacalcet HCl may have x-ray powder diffraction peaks at about 10.6°, 16.4°, 17.1°, and 21.6°±0.2° 2θ. Form II may be considered a chloroform solvate of Cinacalet HCl. This chloroform solvate of Cinacalet HCl may have about 10 to about 30% chloroform or preferably, about 15 to 25% chloroform.

In one embodiment, the invention is directed to crystalline form of Cinacalcet HCl, herein defined as form III, characterized by powder XRD pattern, having four x-ray powder diffraction peaks selected from the following: about 13.8, 17.7°, 19.6°, 20.4°, and 23.5°±0.2° 2θ. The crystalline form of Cinacalcet HCl may be characterized by a powder XRD pattern, with x-ray powder diffraction peaks at about 13.8° and 17.7°, 20.4° and 23.5°±0.2° 2θ. Alternatively, the crystalline form of Cinacalcet HCl may be characterized by a powder XRD pattern, with x-ray powder diffraction peaks at about 17.7°, 19.6°, 20.4° and 23.5°±0.2° 2θ

In another embodiment the present invention encompasses a process for preparing crystalline Cinacalcet HCl Form I by heating Cinacalcet HCl form III, preferably at about 30 to 60° C.

In another embodiment of the invention the present invention encompasses pharmaceutical compositions comprising Cinacalcet HCl Form II or III, wherein the formulation is substantially stable against physical and chemical transformation or the formulation is manufactured in accordance with acceptable GMP requirements.

In yet another embodiment of the invention the present invention encompasses any pharmaceutical compositions comprising Form III. The composition is preferably substantially stable against physical and chemical transformation, for example transformation into other polymorphic forms. The formulation is manufactured in accordance with acceptable GMP requirements.

DETAILED DESCRIPTION OF THE INVENTION

The present invention provides crystalline forms II and III of Cinacalcet hydrochloride, and processes for preparing them, mixtures thereof, and stable pharmaceutical compositions based thereon. Each of the new forms is differentiated by a unique powder X-ray diffraction pattern, a DSC thermogram and TGA thermogram.

Figure 1:
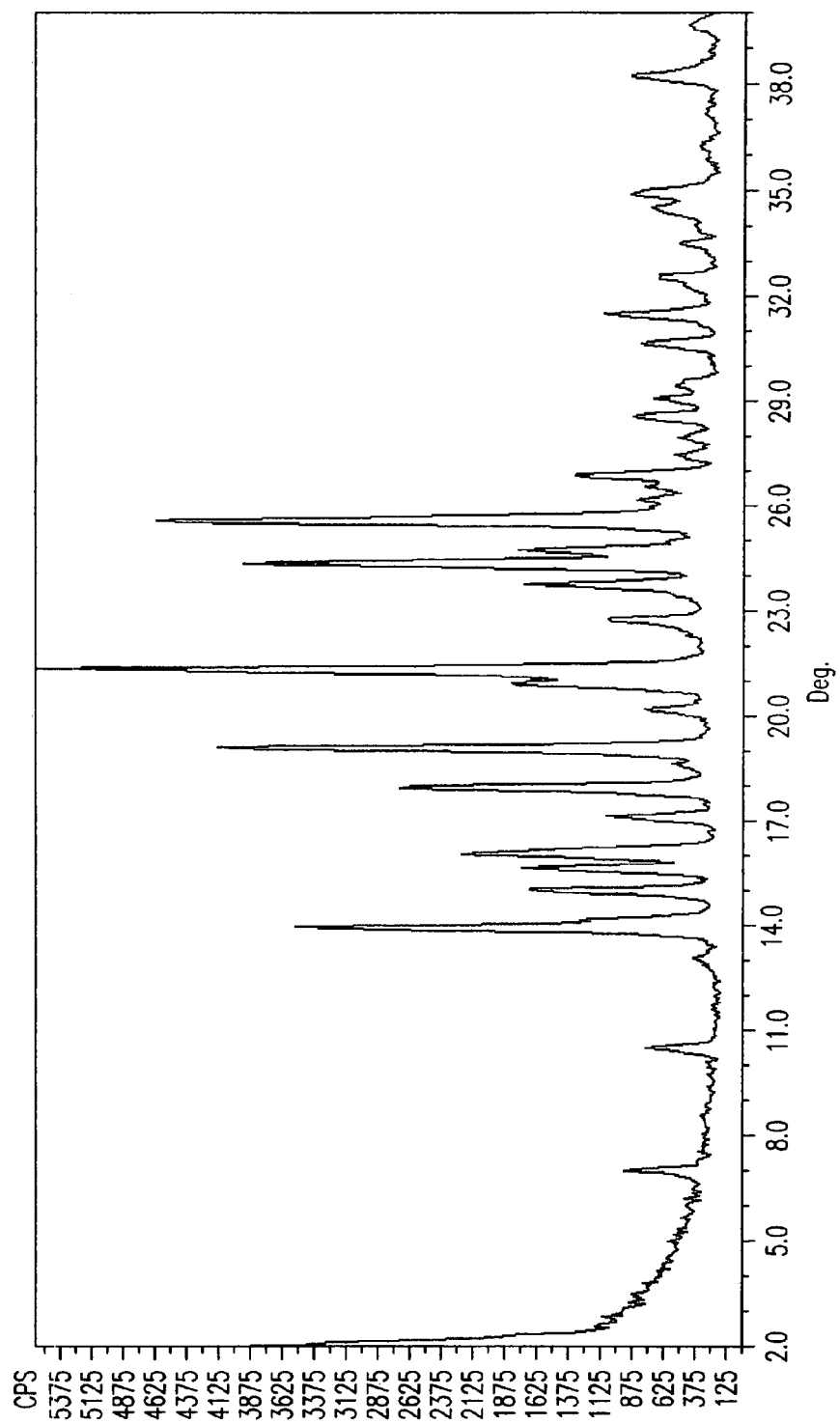
FIG. 1 illustrates an X-Ray Powder Diffraction pattern of Cinacalcet HCl form I.
Figure 4:
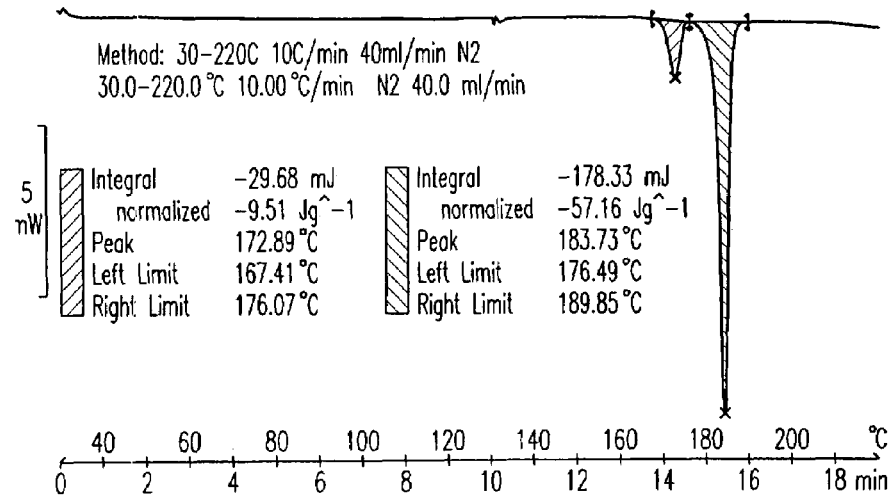
FIG. 4 illustrates a DSC thermogram of Cinacalcet HCl form I.
Figure 7:
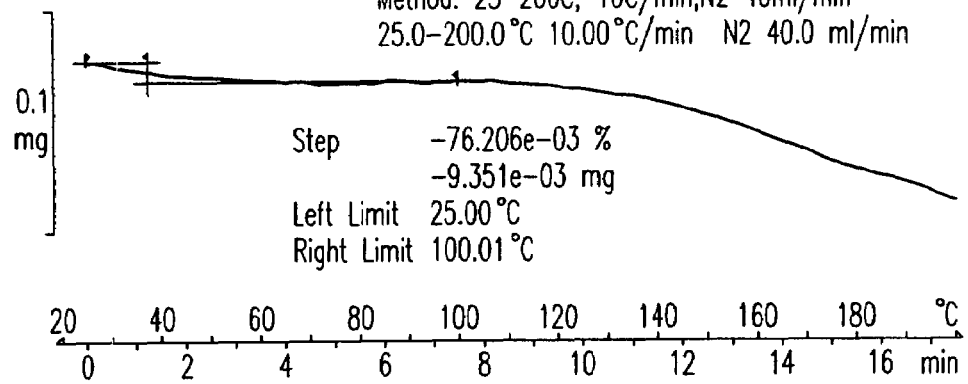
FIG. 7 illustrates a TGA thermogram of Cinacalcet HCl form I.

In the published Summary Basis for Approval of New Drug Application #21688, it is mentioned that Cinacalcet hydrochloride has only one stable crystalline form at ambient temperature. This form is designated herein as Form I and is characterized by a powder XRD peaks at about: 13.9, 19.0, 21.3, 25.5±0.2 deg. 2θ. The crystalline Form I may be further characterized by a PXRD pattern with peaks at about: 15.0, 15.5, 16.0, 17.9, 23.7, and 24.3° 2θ±0.2 deg. 2θ. The XRD pattern of Crystalline Form I is substantially depicted in FIG. 1. Differential Scanning Calorimetry (DSC) thermogram of Cinacalcet HCl form I shows two endotherms at about 160°-170° C. and at about 175°-185° C. The DSC pattern for this form is substantially depicted in FIG. 4. TGA thermograms show weight loss of less than 1% for Form I, thus, this form may be considered as anhydrous. The TGA thermogram for this form is substantially as depicted in FIG. 7.

As used throughout herein, the term "ambient temperature" refers to room temperature. Preferably, the term "ambient temperature" refers to a temperature of from about 18° C. to about 28° C., preferably about 20° C. to about 25° C.

The Cinacalcet hydrochloride [HCl] used to prepare the crystalline forms described may be prepared according to any method known in the art such as the one described in a co-pending U.S. application Ser. No. 11/435,430, and U.S. Pat. No. 6,211,244, which are incorporated herein by reference, as well as Examples 1 and 2.

Figure 5:
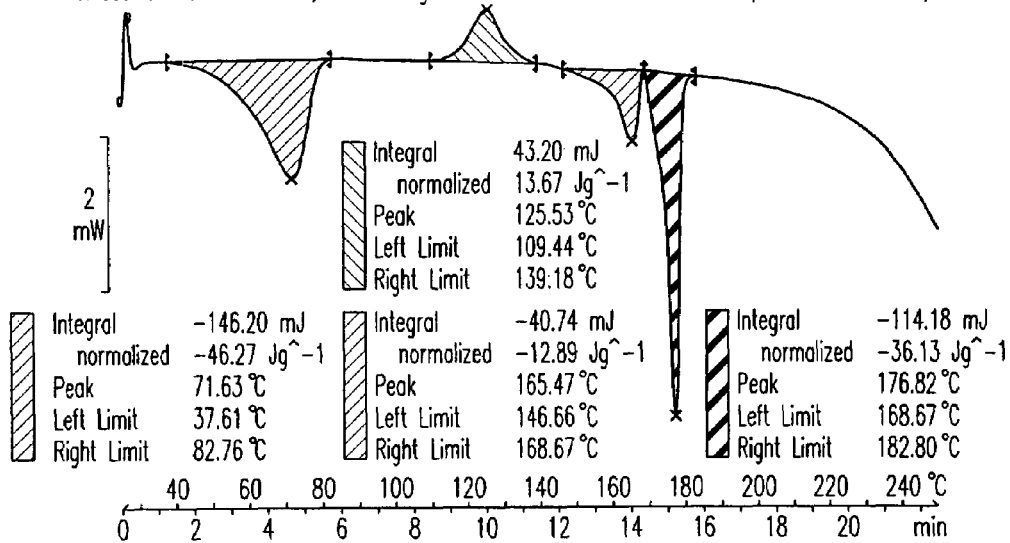
FIG. 5 illustrates a DSC thermogram of Cinacalcet HCl form II.

In one embodiment, the invention is directed to crystalline form of Cinacalcet HCl, herein defined as form II, characterized by a powder XRD pattern, having four x-ray powder diffraction peaks selected from the following: about 10.6°, 13.9°, 16.4°, 17.1°, and 21.6°±0.2° 2θ. The crystalline form of Cinacalcet HCl may have x-ray powder diffraction peaks at about 10.6°, 13.9°, 17.1°, and 21.6°±0.2° 2θ. The crystalline may be further characterized by x-ray powder diffraction peaks at about 16.4, 17.9°, 20.4°, 23.8°, and 24.8°±0.2° 2θ. Alternatively, the crystalline form of Cinacalcet HCl may have x-ray powder diffraction peaks at about 10.6°, 16.4°, 17.1° and 21.6°±0.2° 2θ, in which case, the crystalline form of Cinacalcet HCl may be further characterized by x-ray powder diffraction peaks at about 13.9, 17.9°, 20.4°, 23.8°, and 24.8°±0.2° 2θ. XRD pattern of crystalline Form II is substantially depicted in FIG. 2. Cinacalcet HCl form II may have one DSC endothermic peak at about 72° C., which indicates a solvent removal, an exothermic peak at about 125° C., and two additional endothermic peaks at about 165° C. and about 175°-185° C. The DSC thermogram for this form is substantially as depicted in FIG. 5. Cinacalcet HCl form II may show weight loss at around 18%, as detected by TGA. The TGA thermogram for this form is substantially depicted in FIG. 8. Water content, as was measured by KF titration method was less than about 1%. Form II may be considered a chloroform solvate of Cinacalet HCl. This chloroform solvate of Cinacalet HCl may have about 10 to about 30% chloroform or preferably, about 15 to 25% chloroform.

In another embodiment, the present invention encompasses a process for preparing crystalline Cinacalcet HCl Form II comprising providing a solution of Cinacalet HCl and Chloroform, preferably at ambient temperature; admixing n-Pentane to obtain precipitated Form II. The precipitate may be maintained as a slurry, for example, by stirring for about 5 minutes to 6 hours, preferably about 5 minutes to about two hours, more preferably about 5 minutes to about 15 minutes. Preferably, maintaining the slurry is at about room temperature. Form II is then recovered by any method known in the art, preferably by filtration.

In another embodiment, the present invention encompasses another process for preparing crystalline Cinacalcet HCl Form II comprising providing a solution of Cinacalcet HCl and Chloroform, preferably at ambient temperature, and admixing n-Heptane to obtain a precipitate. The precipitate is then stirred within the reaction mixture for at least 8 hours, preferably for about 8 to 24 hours, more preferably about 12 to 18 hours, more preferably about 16 hours. The form II is then recovered by any method known in the art, preferably by filtration.

In one embodiment, the invention is directed to crystalline form of Cinacalcet HCl, herein defined as form III, characterized by powder XRD pattern, having four x-ray powder diffraction peaks selected from the following: about 13.8, 17.7°, 19.6°, 20.4°, and 23.5°±0.2° 2θ. The crystalline form of Cinacalcet HCl may be characterized by a powder XRD pattern, with x-ray powder diffraction peaks at about 13.8° and 17.7°, 20.4° and 23.5°±0.2° 2θ and may be optionally further characterized by x-ray powder diffraction peaks at about 7.0°, 13.8°, 15.7°, 16.2° and 19.6°±0.2° 2θ. Alternatively, the crystalline form of Cinacalcet HCl may be characterized by a powder XRD pattern, with x-ray powder diffraction peaks at about 17.7°, 19.6°, 20.4° and 23.5°±0.2° 2θ and optionally further characterized by x-ray powder diffraction peaks at about 7.0°, 13.8°, 15.7°, and 16.2°±0.2° 2θ. The powder XRD pattern of Form III is substantially depicted in FIG. 3. The DSC thermogram of Form III is substantially depicted in FIG. 6. Cinacalcet HCl Form IEI shows two endothermic peaks at about 160°-170° C., and about 175°-185° C. Weight loss of less than 1% was detected by TGA. The TGA of Form III is substantially depicted in FIG. 9. This form may be considered anhydrous.

In yet another embodiment, the present invention encompasses a process for preparing crystalline Cinacalcet HCl Form III comprising providing a solution of Cinacalet HCl and Chloroform; inducing precipitation by cooling or admixing water to obtain a precipitate. The precipitate may be stirred with the reaction mixture at ambient temperature, preferably for about 2 to about 4 days, preferably about 3 days. The form III is then recovered by any method known in the art, preferably by filtration.

In yet another embodiment, the present invention encompasses a process for preparing crystalline Cinacalcet HCl Form III comprising dissolving Cinacalet HCl in Chloroform, preferably at ambient temperature, and adding n-Heptane to obtain a precipitate. Preferably, the precipitate is stirred with the reaction mixture at ambient temperature, preferably for less than 6 hours, preferably about 1 minute to 4 hours, more preferably for about 4 to 15 minutes. The form III is then recovered by any method known in the art, preferably by filtration.

In another embodiment the present invention encompasses a process for preparing crystalline Cinacalcet HCl Form I by heating Cinacalcet HCl form III, preferably at about 30 to 60° C., more preferably 40 to 50° C. Heating may be performed for at least about 4 hours, more preferably about 16 to 24 hours. The heating process is preferably conducted in an inert atmosphere. Preferably, the heating is conducted under vacuum.

In another embodiment of the invention the present invention encompasses any pharmaceutical compositions comprising Cinacalcet HCl Form II or III, wherein the formulation is substantially stable against physical and chemical transformation or the formulation is manufactured in accordance with acceptable GMP requirements.

In yet another embodiment of the invention the present invention encompasses any pharmaceutical compositions comprising Form III. The composition is preferably substantially stable against physical and chemical transformation, for example transformation into other polymorphic forms. The formulation is manufactured in accordance with acceptable GMP requirements.

Pharmaceutical formulations/compositions of the present invention contain Cinacalcet HCl Form II or III. In addition to the active ingredient(s), the pharmaceutical formulations of the present invention may contain one or more excipients. Excipients are added to the formulation for a variety of purposes. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. EUDRAGIT®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, Cinacalcet HCl Form II or III, and any other solid excipients are dissolved or suspended in a liquid carrier such as water, vegetable oil, alcohol, polyethylene glycol, propylene glycol or glycerin.

Liquid compositions may also be dyed using any pharmaceutically acceptable colorant to improve their appearance and/or facilitate patient identification of the product and unit dosage level.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

The solid compositions of the present invention may include powders, granulates, aggregates and compacted compositions. The dosages include dosages suitable for oral, buccal, rectal, parenteral (including subcutaneous, intramuscular, and intravenous), inhalant and ophthalmic administration. The most suitable administration in any given case will depend on the nature and severity of the condition being treated. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs. The dosage form may be a capsule containing the composition, such as a powdered or granulated solid composition, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art. A composition for tableting or capsule filling may be prepared by wet granulation. In wet granulation, some or all of the active ingredients and excipients in powder form are blended and then further mixed in the presence of a liquid, typically water, which causes the powders to clump into granules. The granulate is screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting A capsule filling of the present invention may comprise any of the aforementioned blends and granulates that were described with reference to tableting, however, they are not subjected to a final tableting step.

Cinacalcet HCl Form II or III is administered to a mammal, preferably a human in need thereof, to inhibit platelet aggregation and reduce the chance of a primary or secondary ischemic event such as a heart attack or stroke.

EXAMPLES

Instrumentation

PXRD

X-Ray powder diffraction data were obtained using a SCINTAG powder X-Ray diffractometer model X'TRA equipped with a solid state detector and a variable gonimeter. Copper radiation of 1.5418 Å was used. A round standard aluminum sample holder with round zero background, and cavity of 25(diameter)*0.5(depth) mm. Scanning parameters range of: 2-40 deg. 2θ and continuous scan rate of 3 deg./min.

Thermal Analysis

Differential Scanning Calorimetry (DSC) analysis was done using a Mettler Toledo 821 Star$^e$. The crucible was crimped and punched prior to analysis. The weight of the samples was about 3-5 mg; the samples were scanned at a rate of 10° C./min from 30° C. to 250° C. The oven was constantly purged with nitrogen gas at a flow rate of 40 mL/min. Standard 40 μl aluminum crucibles covered by lids with 3 holes were used.

Thermal weight change measurements were made on a Mettler TG50 Thermogravimetric Analyzer (TGA). Samples of 7-15 mg were placed in an aluminum pan and placed in the device. The data was collected from about 50° C. to about 350° C. at a rate of 10° C./min.

Example 1

Preparation of Cinacalcet Base 25.5 gr of (2E)-3-[3-(trifluoromethyl)phenyl]prop-2-en-1-ol were dissolved in Acetonitrile (204 ml). (R)-1-Naphtylethyl amine (14.5 ml) and anhydrous $K_2CO_3$ (24.9 gr) were added and the reaction mixture was heated to reflux temperature for 16 hours. Then salts were filtered out and the solvent was removed under reduced pressure. The residue was dissolved in toluene (75 ml) and the solution was heated to 70° C. The obtained solution was washed with 0.2N aqueous HCl solution (pH=1), water, a saturated solution of $NaHCO_3$ (pH=8-9) and finally with water. The organic phase was dried over $Na_2SO_4$ (optionally), filtered and the solvent was evaporated until dryness to obtain 33.4 gr of Cinacalcet base.

Example 2

Preparation of Cinacalcet HCl

Cinacalcet base (0.8 gr) was dissolved in MTBE (50 ml) at room temperature. Then HCl gas was bubbled into the solution. The solution was stirred at room temperature for 0.5 hour to obtain precipitate. The product was isolated by filtration, washed with MTBE (8 ml) and dried at 50° C. in a vacuum oven for 15 hours to obtain 0.5 gr of Cinacalcet hydrochloride.

Example 3

Preparation of Cinacalcet HCl Form II 0.52 gr of Cinacalcet HCl was dissolved in Chloroform (3.5 ml) at room temperature. Then n-Pentane (30 ml) was added in one portion to obtain a precipitate. The slurry was stirred at room temperature for 5 minutes. The solid was then isolated by filtration to obtain Cinacalcet HCl crystal form II.

Example 4

Preparation of Cinacalcet HCl Form II 0.58 gr of Cinacalcet HCl was dissolved in Chloroform (6 ml) at room temperature. Then n-Heptane (30 ml) was added in one portion to obtain a precipitate. The slurry was stirred at room temperature for 16 hours. The solid was then isolated by filtration to obtain Cinacalcet HCl crystal form II.

Example 5

Preparation of Cinacalcet HCl Form III 0.5 gr of Cinacalcet HCl was dissolved in Chloroform (3.5 ml) at room temperature. Then water (30 ml) was added in one portion. The mixture was stirred at room temperature for 72 hours. The solid was then isolated by filtration and washed with water (5 ml) to obtain Cinacalcet HCl crystal form III.

Example 6

Preparation of Cinacalcet HCl Form III 0.62 gr of Cinacalcet HCl was dissolved in Chloroform (6 ml) at room temperature. Then n-Heptane (30 ml) was added in one portion to obtain a precipitate. The slurry was stirred at room temperature for 4 minutes. The solid was then isolated by filtration, washed with n-Heptane (1.5 ml) to obtain Cinacalcet HCl crystal form III. The obtained Cinacalcet HCl crystal form III was then dried at 50° C. for 24 hours and the crystalline structure was maintained as form III.

Example 7

Preparation of Cinacalcet HCl Form III

Cinacalcet HCl Form I (5 gr) was stirred in Chloroform (20-23 ml) at room temperature. The mixture was heated to reflux temperature to obtain a clear solution: Then the solution was cooled to room temperature (optional—further cooling can be done using an ice-bath) to obtain a precipitate. The product was isolated by filtration and dried in a vacuum oven at 50° C. for 14-24 hours to obtain 2 gr of Cinacalcet HCl crystal form III.

Example 8

Preparation of Cinacalcet HCl Form I

Cinacalcet HCl form III, prepared according to example 3 was heated at 50° C. under vacuum for 22 hours. Cinacalcet HCl form I was obtained.

Having thus described the invention with reference to particular preferred embodiments and illustrative examples, those in the art would appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. All references mentioned herein are incorporated in their entirety.

What is claimed:

1. A crystalline form of Cinacalcet HCl, characterized by a powder XRD pattern, having x-ray powder diffraction peaks at about 10.6°, 13.9°, 16.4°, 17.1° and 21.6°±0.2° 2θ.

2. The crystalline form of Cinacalcet HCl of claim 1, further characterized by x-ray powder diffraction peaks at about 16.4°, 17.9°, 20.4°, 23.8°, and 24.8°±0.2° 2θ.

3. The crystalline form of Cinacalcet HCl of claim 1, further characterized by x-ray powder diffraction peaks at about 13.9°, 17.9°, 20.4°, 23.8°, and 24.8°±0.2° 2θ.

Figure 2:
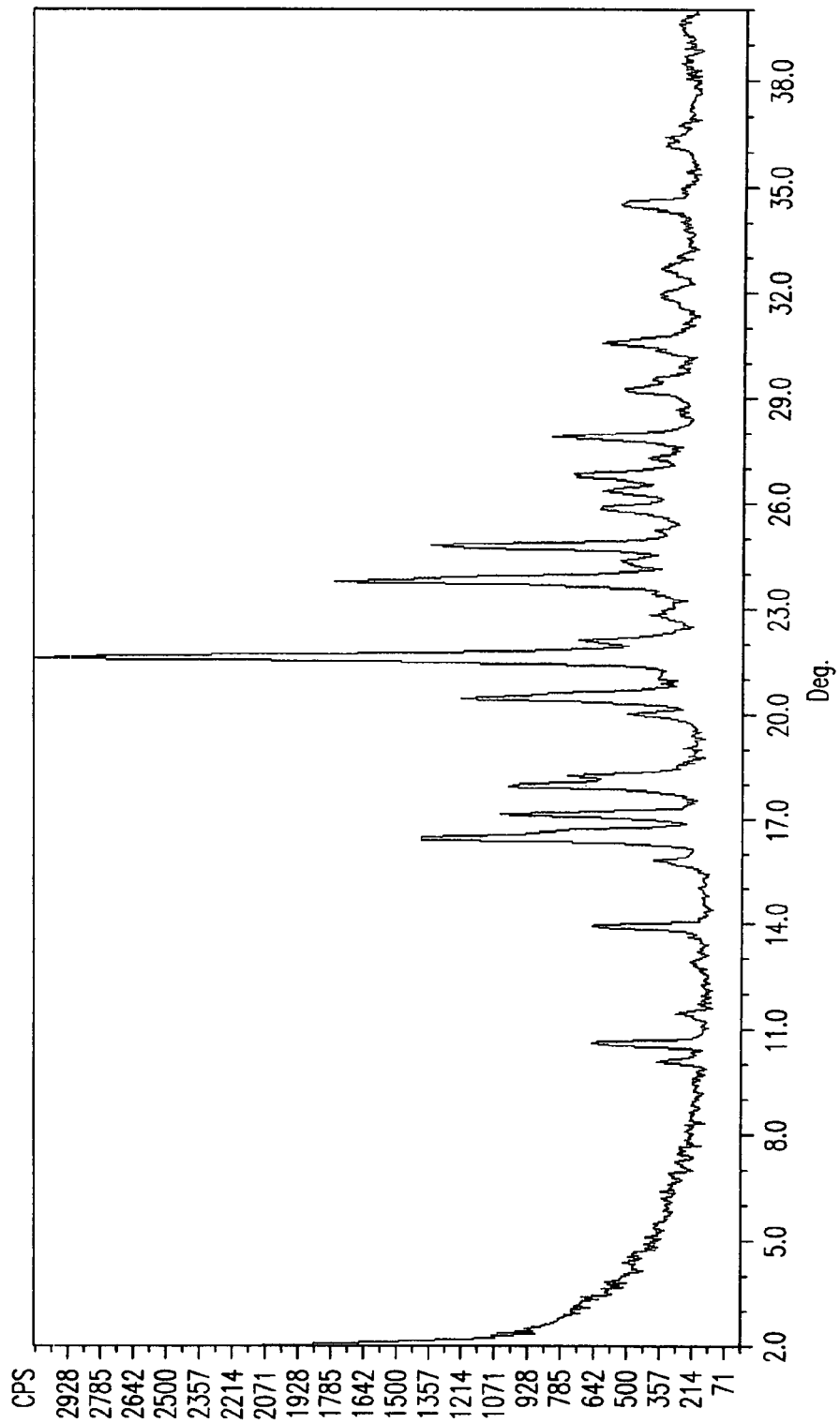
FIG. 2 illustrates an X-Ray Powder Diffraction pattern of Cinacalcet HCl form II.

4. The crystalline form of Cinacalcet HCl of claim 1, characterized by x-ray powder diffraction pattern as depicted in FIG. 2.

5. The crystalline form of Cinacalcet HCl of claim 1, characterized by a DSC thermogram having one endothermic peak at about 72° C., an exothermic peak at about 125° C., and two additional endothermic peaks at about 165° C. and about 175°-185° C.

6. The crystalline form of Cinacalcet HCl of claim 1, characterized by a DSC thermogram as depicted in FIG. 5.

7. The crystalline form of Cinacalcet HCl of claim 1, having a weight loss of about 18%.

Figure 8:
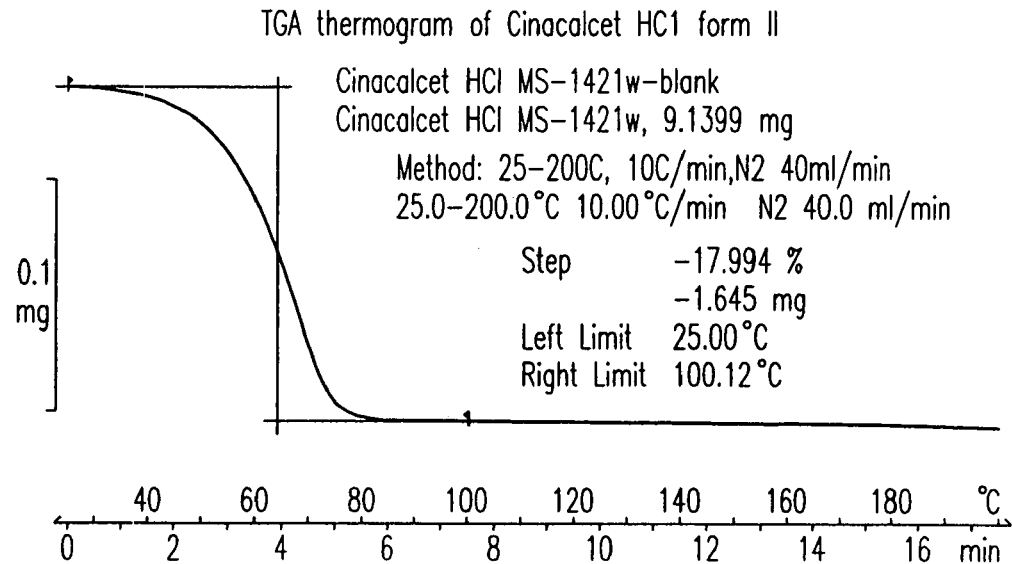
FIG. 8 illustrates a TGA thermogram of Cinacalcet HCl form II.

8. The crystalline form of Cinacalcet HCl of claim 1, having a TGA thermogram as depicted in FIG. 8.

9. The crystalline form of Cinacalcet HCl of claim 1, having less than 1% water content, as measured by KF.

10. A process for the preparation of the Cinacalcet HCl of claim 1 comprising: providing a solution of Cinacalcet HCl and chloroform; admixing n-Pentane to obtain a precipitate; maintaining the slurry for about 5 minutes to about 6 hours; and recovering the Cinacalcet HCl.

11. The process of claim 10 wherein maintaining is for a period of about 5 minutes to about two hours.

12. The process of claim 11 wherein maintaining is for a period of about 5 minutes to about 15 minutes.

13. A process for the preparation of the Cinacalcet HCl of claim 1 comprising: providing a solution by dissolving Cinacalcet HCl in Chloroform; admixing n-Heptane to obtain a slurry; maintaining the slurry for at least 8 hours; and recovering the precipitated Cinacalcet HCl.

14. The process of claim 13 wherein the precipitate obtained is stirred within the reaction mixture for about 8 to 24 hours.

15. The process of claim 14 wherein the precipitate obtained is stirred within the reaction mixture for about 16 to 24 hours.

16. A crystalline form of Cinacalcet HCl, characterized by a powder XRD pattern, having x-ray powder diffraction peaks at about 13.8°, 17.7°, 19.6°, 20.4° and 23.5°±0.2° 2θ.

17. The crystalline form of Cinacalcet HCl of claim 16, further characterized by x-ray powder diffraction peaks at about 7.0°, 13.8°, 15.7°, 16.2° and 19.6°±0.2° 2θ.

18. The crystalline form of Cinacalcet HCl of claim 16, further characterized by x-ray powder diffraction peaks at about 7.0°, 13.8°, 15.7°, and 16.2°±0.2° 2θ.

Figure 3:
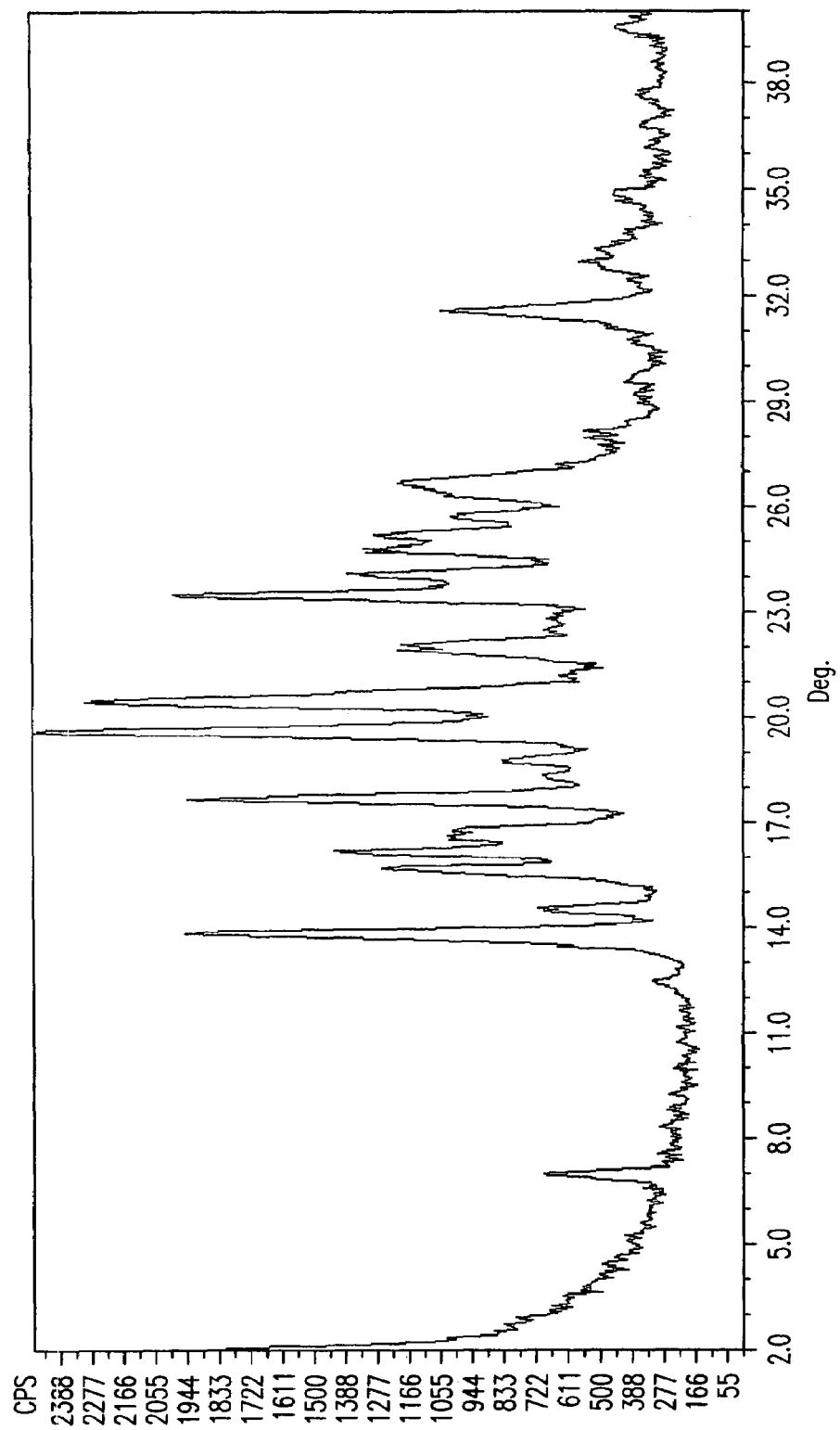
FIG. 3 illustrates an X-Ray Powder Diffraction pattern of Cinacalcet HCl form III.

19. The crystalline form of Cinacalcet HCl of claim 16, further characterized by x-ray powder diffraction pattern as depicted in FIG. 3.

20. The crystalline form of Cinacalcet HCl of claim 16, further characterized by a DSC thermogram having two endothermic peaks at about 160°-170° C., and about 175°-185° C.

Figure 6:
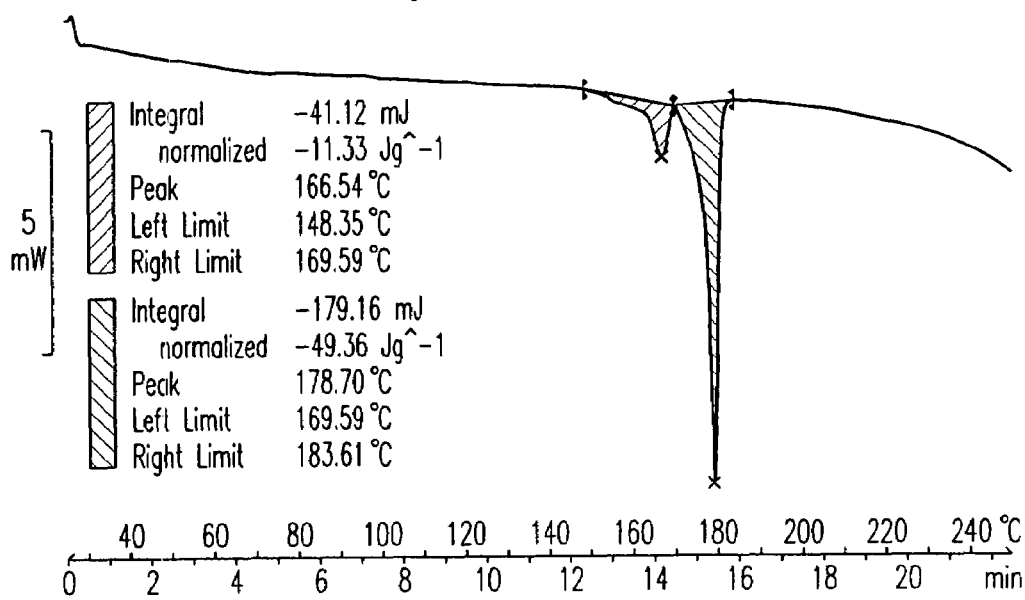
FIG. 6 illustrates a DSC thermogram of Cinacalcet HCl form III.

21. The crystalline form of Cinacalcet HCl of claim 16, characterized by a DSC thermogram substantially as depicted in FIG. 6.

22. The crystalline form of Cinacalcet HCl of claim 16, having a weight loss of less than 1%.

Figure 9:
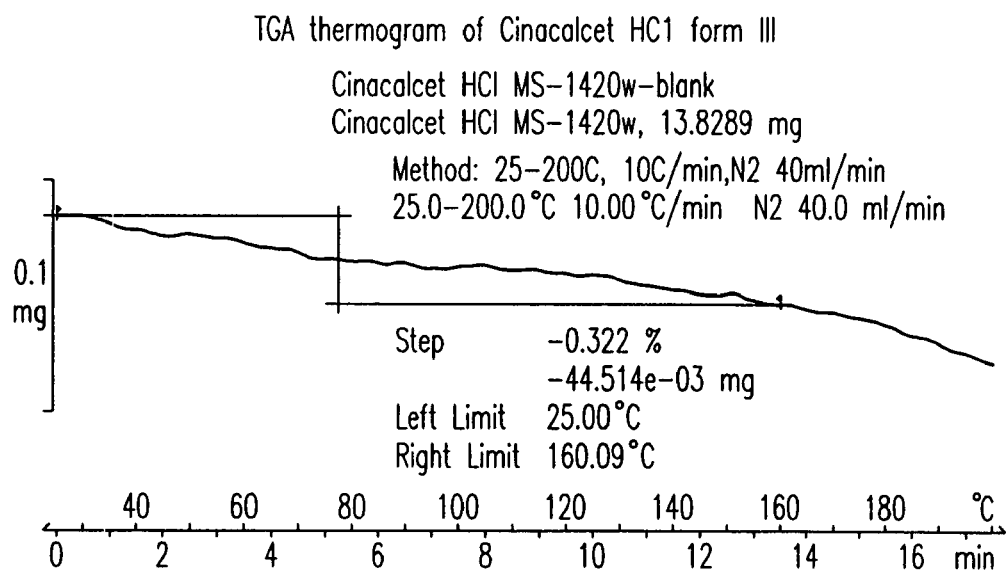
FIG. 9 illustrates a TGA thermogram of Cinacalcet HCl form III.

23. The crystalline form of Cinacalcet HCl of claim 16, having a TGA thermogram as depicted in FIG. 9.

24. A process for preparing the crystalline form of Cinacalcet HCl of claim 16, comprising providing a solution of Cinacalcet HCl and chloroform, and inducing precipitation by cooling or admixing water to obtain a precipitate.

25. The process of claim 24, wherein Cinacalcet HCl in chloroform is heated followed by cooling.

26. The process of claim 24, further comprising stirring at ambient temperature.

27. The process of claim 26 wherein stirring is for about three days.

28. A process for preparing the crystalline form of Cinacalcet HCl of claim 16, comprising: dissolving Cinacalcet HCl in chloroform; admixing n-heptane to obtain mixture; and maintaining the mixture for less than 6 hours to obtain Form III.

29. The process of claim 28, wherein the Cinacalcet HCl is added to the chloroform at ambient temperature.

30. The process of claim 28, wherein maintaining is by stirring for about 1 minute to about 4 hours.

31. The process of claim 28, wherein maintaining is by stirring for about 4 to about 15 minutes.

32. A process for the preparation of Cinacalcet HCl Form I, characterized by x-ray powder diffraction peaks at about 13.9°, 19.0°, 21.3°, 25.5°±0.2° 2θ, comprising heating a crystalline form of Cinacalcet HCl characterized by a powder XRD pattern, having four x-ray powder diffraction peaks selected from the following: about 13.8°, 17.7°, 19.6°, 20.4° and 23.5°±0.2° 2θ.

33. The process of claim 32, wherein the Cinacalcet HCl is heated at about 30° to about 60° C.

34. The process of claim 33, wherein the Cinacalcet HCl is heated at about 40° to about 50° C.

35. The process of claim 32, wherein the Cinacalcet is heated for at least 4 hours.

36. The process of claim 32, wherein the Cinacalcet is heated for about 16 to about 24 hours.

37. A pharmaceutical solid composition, comprising the Cinacalcet HCl Form II, characterized by x-ray powder diffraction peaks at about 10.6°, 13.9°, 16.4°, 17.1°, 21.6°±0.2° 2θ, or III, characterized by x-ray powder diffraction peaks at about 13.8°, 17.7°, 19.6°, 20.4°, 23.5°±0.2° 2θ, and at least one pharmaceutically acceptable excipient.

* * * * *